United States Patent
Harper et al.

(10) Patent No.: US 6,500,188 B2
(45) Date of Patent: Dec. 31, 2002

(54) ULTRASONIC SURGICAL INSTRUMENT WITH FINGER ACTUATOR

(75) Inventors: Richard M. Harper, Cincinnati, OH (US); Paul M. Miklautsch, Shakope, MN (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/772,015

(22) Filed: Jan. 29, 2001

(65) Prior Publication Data

US 2002/0103496 A1 Aug. 1, 2002

(51) Int. Cl.⁷ ............................................... A61B 17/32
(52) U.S. Cl. ........................................................ 606/169
(58) Field of Search ............................... 606/1, 51, 52, 606/154, 169, 174, 205–210

(56) References Cited

U.S. PATENT DOCUMENTS

| | | | |
|---|---|---|---|
| 4,433,687 A | * 2/1984 | Burke et al. ................. | 606/174 |
| 5,257,988 A | 11/1993 | L'Esperance, Jr. | |
| 5,300,081 A | 4/1994 | Young et al. | |
| 5,368,605 A | * 11/1994 | Miller, Jr. .................... | 606/170 |
| 5,514,157 A | * 5/1996 | Nicholas et al. ............. | 606/205 |
| 5,549,637 A | * 8/1996 | Crainich ...................... | 606/207 |
| 5,700,275 A | * 12/1997 | Bell et al. .................... | 606/208 |
| 5,873,873 A | 2/1999 | Smith et al. | |
| 5,976,121 A | * 11/1999 | Matern et al. ............... | 606/174 |
| 6,004,335 A | 12/1999 | Vaitekunas et al. | |
| 6,063,098 A | * 5/2000 | Houser et al. ............... | 606/169 |

FOREIGN PATENT DOCUMENTS

EP 0544882 B1 * 10/1997 ........... A61B/17/28

* cited by examiner

Primary Examiner—Marvin M. Lateef
Assistant Examiner—Eleni Mantis Mercader
(74) Attorney, Agent, or Firm—Verne E. Kreger, Jr.

(57) ABSTRACT

An ultrasonic surgical instrument having a handle with a finger actuator, and more particularly, an ultrasonic surgical device adapted to be held by a surgeon and fingers-operated with precise movements while opening and closing an ultrasonic instrument while meeting the ergonomic requirements of the surgeon with regard to comfort and imparting the surgeon with an enhanced dextral control for easy maneuverability of the instrument. The instrument incorporates a thimble-shaped lever at the distal end of the handle for actuating the clamp arm of the ultrasonic surgical instrument, and votator structure for selective rotation of the surgical device whereby the ergonomic thimble-shaped lever and pencil grip provide the physician with an improved degree of control, greater comfort in manipulating the instrument, and the ability to perform blunt dissections.

8 Claims, 2 Drawing Sheets

ULTRASONIC SURGICAL INSTRUMENT WITH FINGER ACTUATOR

BACKGROUND OF THE INVENTION

1. Field of the invention

The present invention relates to an ultrasonic surgical instrument with a finger actuator, and more particularly, relates to an ultrasonic surgical device adapted to be held by a surgeon and operated with precise movements while opening and closing an ultrasonic instrument while meeting the ergonomic requirements of the surgeon with regard to comfort and imparting the surgeon with an enhanced dextral control for easy maneuverability of the instrument.

2. Discussion of the Prior Art

Presently, a wide variety of surgical instruments of the type under consideration are disclosed in the state-of-the-technology which are intended to provide diverse kinds of actuating mechanisms in the use of ultrasonic surgical instruments by surgeons and other medical practitioners for the treatment of patients.

Vaitekunas et al., U.S. Pat. No. 6,004,335, which is commonly assigned to the assignee of the present application, discloses an ultrasonic surgical instrument having an actuating element in a handle portion which is operatively coupled to at least one of two effector elements located at a distal end of the instrument. The actuating element is arranged to move at least one effector element towards the other effector element so as to engage tissue of a patient between the first and second effector elements. A cutting element is coupled to the distal end of an inner shaft in order to cut and/or cauterize tissue which is engaged by the first and second effector elements. Pursuant to the present invention, the actuating element possesses the form of a thimble-shaped lever in which a finger is inserted, whereas the patent discloses the actuating element as a sliding lever. In the present invention, the actuating element moves up and down, in the same direction as a clamp arm to provide for logical and convenient movement of the effector element, whereas the patent has an actuator which slides distally to proximally and then reveresly proximally to distally. Accordingly, pursuant to the inventive actuating element, the surgeon is provided with a more logical and ergonomically convenient actuator which moves in an entirely new way and direction in comparison with the prior art.

Shibata Yoshikiyo Japanese Unexamined Patent Application 2000-41990 discloses an ultrasonic surgical instrument with a thumb activated actuator which is located on the distal end of a handle. The handle is held with the palm down using the fingers to support the underside leaving the thumb free to work the actuator. When the actuator is pushed up by the thumb, the clamp assembly is opened away from the fixed blade, whereas upon the actuator being pushed down by the thumb, the clamp closes. A skid pad is present on the actuator to reduce slippage of the physicians thumb. In contrast, the present invention is designed to alleviate the problem of physician fatigue caused by other hand held instruments from having the fingers held awkwardly during lengthy surgery. The present invention uses a pencil grip rather than the palms down grip providing the surgeon with a more familiar grip which may be held for long periods of time. The ribbed slip guard effectively reduces fatigue while increasing surgical accuracy, and additionally the actuator of the present invention is thimble shaped, and provides for the more versatile pencil grip with the actuator worked by the index finger. Smith et al. U.S. Pat. No. 5,873,873 discloses an ultrasonic surgical device where selective, indexed rotational positioning of the clamping mechanism and end effector is achieved by the provision of a detent mechanism incorporated into a clamp drive mechanism of the apparatus. Rotation is facilitated by a rotational knob located at the distal end of the handle portion of the ultrasonic instrument. Contrastingly, in the present invention, the rotation knob is located towards the center of the handle inside the handle, with the rotational knob being exposed through the two indents. Consequently, the rotation of the knob and therefore of the tip/clamp assembly is facilitated by the positioning of the rotation knob within and towards the center of the handle. The center position is more desirable because it allows the surgeon to rotate the knob with the same hand he is holding the ultrasonic surgical instrument with. Due to the pencil-grip which is used with this instrument, the surgeons do not need to use a second hand to rotate the knob, he merely uses the thumb and ring fingers of the hand holding the instrument.

Young et al. U.S. Pat. No. 5,300,081 discloses a surgical instrument control means for selecting between a first mode of operation in which the advancement of a surgical clip from a storage into the jaw members is initiated by the user, and a second mode in which the advancement of the surgical clips is initiated independently of the user. This instrument it is not ultrasonic, and does not use a finger operated lever to actuate a tip assembly. Although the instrument has a finger operated slide, this slide functions as a selector between two different modes of the function, and does not actuate the tip assembly. The finger slide more closely resembles a slide on a rifle used to choose automatic or semi-automatic rather than the clamp actuator pursuant to the present invention. L'Esperance, Jr. U.S. Pat. No. 5,257,988 discloses a surgical instrument in which a lever system is utilized in order to actuate the forward displacement of a sleeve over a port. Pushing down on the level actuates the sleeve over the port, whereas a spring automatically biases the lever to its upright return position and resultingly exposes the port. In contrast, the present invention uses a lever system to open and close a clamp arm rather than to slide a sleeve into a closed position. This in effect, allows a surgeon to apply force to the lever in both the upward and downward direction for greater control of the clamp, unlike the prior art which can only be pushed down by the surgeon. The patent also fails to disclose an ergonomically shaped thimble-lever to provide more comfort to the surgeon, nor does it display a pencil-grip which offers ergonomic comfort and greater maneuverability to a user. In the patent, the instrument is held with the palm down, requiring the thumb to actuate the lever, whereby the palm-down position decreases both comfort and maneuverability in operating the instrument.

SUMMARY OF THE INVENTION

The foregoing drawbacks and limitations which are encountered in the prior art are clearly obviated by the present inventive ultrasonic surgical instrument by providing a finger actuated mechanism which meets the ergonomic requirements of a surgeon or medical practitioner.

Pursuant to the invention, the surgical instrument essentially consists of an ultrasonic surgical device with a blade-like tip and clamp arm, which is held with a handle by the physician or surgeon with a pencil grip. The instrument incorporates a novel thimble-shaped lever at the distal end of the handle for actuating the clamp arm of the ultrasonic surgical instrument, whereby the ergonomic thimble-shaped lever and pencil grip provide the physician with an improved degree of control, greater comfort in manipulating the instrument, and the ability to perform blunt dissections.

The present invention features a surgical instrument of the type described, possessing a pencil grip which provides the physician or surgeon using the ultrasonic surgical device with a familiar grip which allows for finer and more precise motor movements, and therefore an enlarged degree of control in using the instrument. The present invention also employs a thimble-shaped lever which allows the physician or surgeon to apply force to both open and close the clamp arm, in contrast with many prior art devices which function in a spring-loaded operating mode. This imparts the physician with an improved control over the instrument, and also allows him to perform blunt dissections by employing the thimble-shaped lever. The ergonomic design of the thimble-shaped lever results in a greater degree of comfort to the surgeon by reducing stress on the pressure points on the hand of the surgeon. This unique aspect, combined with the fact that the surgeon or practitioner does not have to apply pressure against a spring-loaded actuating system, decreases the occurrence and intensity of any fatigue encounter during lengthy operating procedures utilizing the present ultrasonic surgical instrument.

A handle in the form of a shroud for an ultrasonic surgical instrument incorporating a clamp and blade device is held by a surgeon or medical practitioner like a pencil with a thimble-shaped operating lever being located at the distal end of the handle, whereby the surgeon or practitioner, i.e. physician or nurse, positions an index finger into the lever interior while using the instrument.

Moving the finger, and consequently the lever in an upward direction relative to the longitudinal axis of the instrument, results in the clamp assembly opening upwardly. The lowering of the finger then lowers the clamp arm into a closed position with the fixed blade, as a consequence of which the clamp arm moves in the same direction as the finger operating the lever. The handle is also ergonomically designed to meet the needs of the surgeon or practitioner operating the ultrasonic device, and wherein the pencil grip of the handle provides surgeons with a familiar gripping position to facilitate an increased accuracy in the use of the instrument. The surgical instrument also enables the surgeon or physician to perform blunt dissections by applying force which is adapted to both open and close the instrument, whereas blunt dissection cannot be readily accomplished by means of instruments which possess a spring-loaded actuating lever. The design of the inventive ultrasonic surgical instrument focuses on imparting surgeons with a greater degree of dextral control by enabling them to use large muscle groups to grippingly hold and support the instrument, and fine motor skills to precisely operate the thimble-shaped lever.

In addition, pursuant to a further inventive feature, enabling concurrent rotation of a rotator arrangement located within the handle which enables selective rotational movement of the clamp arm, and resultingly clamp and blade device, about the longitudinal axis of the instrument.

Accordingly, it is an object of the present invention to provide an ultrasonic surgical instrument which is operable by a surgeon or medical practitioner through a finger-actuated lever mechanism while held in a pencil-like gripped position.

Another object is to provide an ultrasonic surgical instrument of the type described which facilitates precise selective clamping and/or rotational operation of cooperating cam and blade component while meeting the ergonomic requirements of the surgeon or medical practitioner employing the instrument.

A further object of the invention resides in the provision of a method for the utilization of an ultrasonic surgical instrument which includes thimble-shaped finger-operated lever mechanism in conformance with the ergonomic needs of a surgeon or medial practitioner.

BRIEF DESCRIPTION OF THE DRAWINGS

Reference may now be made to the following detailed description of a preferred embodiment of the invention, taken in conjunction with the accompanying drawings; in which.

DETAILED DESCRIPTION OF A PREFERRED EMBODIMENT

Figure 1:
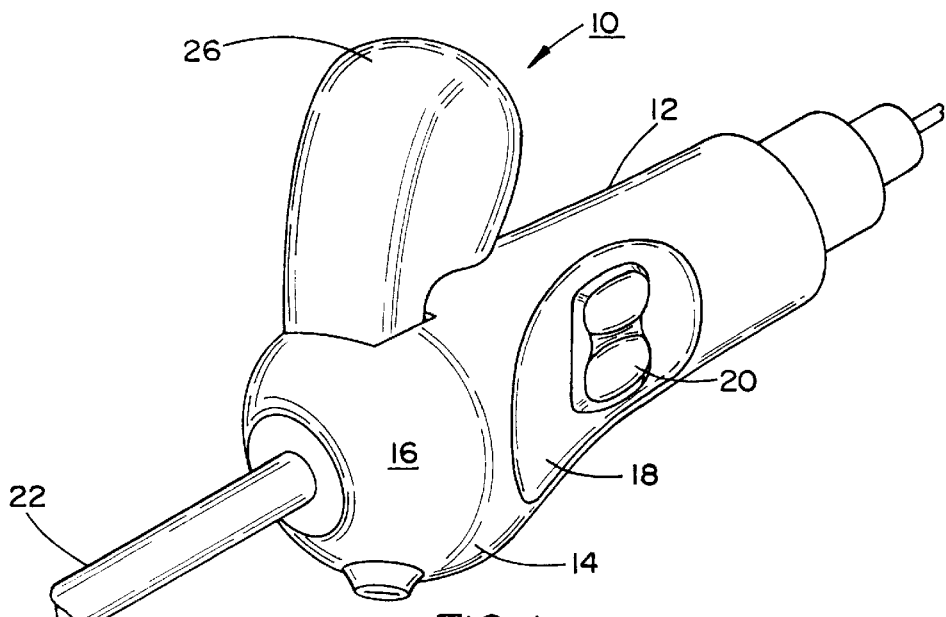
FIG. 1 illustrates, generally schematically, a perspective representation of the operating handle portion of an ultrasonic surgical instrument which possesses a finger-operated lever mechanism for actuation of the operative portions of the instrument, pursuant to the invention.
Figure 2:
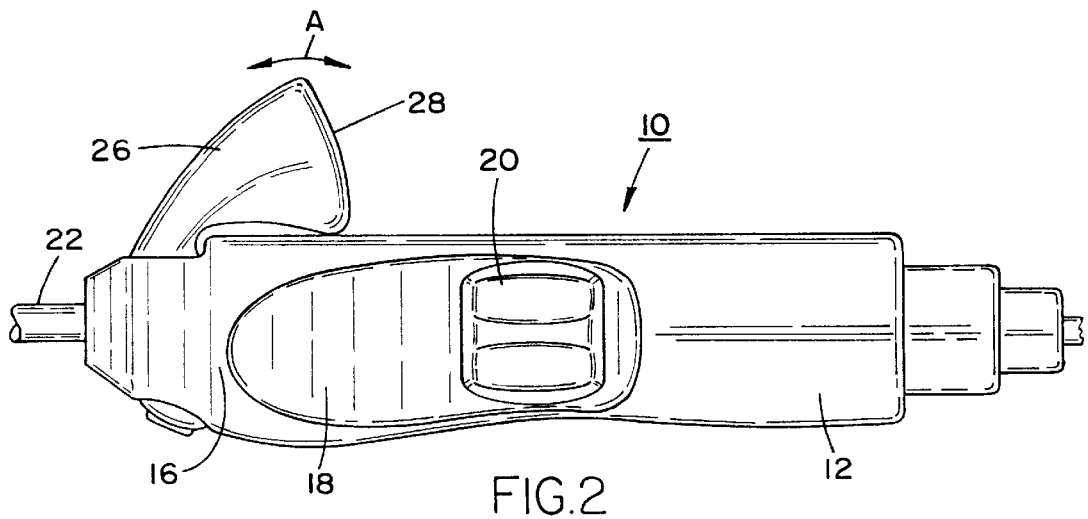
FIG. 2 illustrates a side view of the operating handle portion showing FIG. 1.
Figure 3:
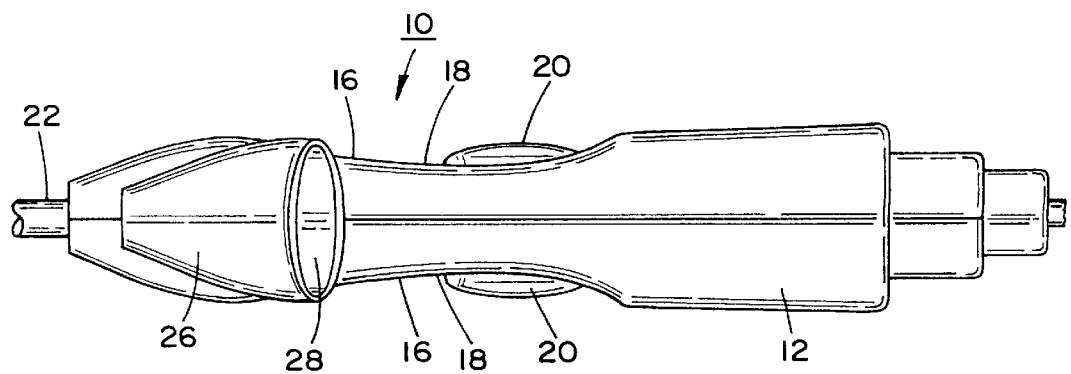
FIG. 3 illustrates a top plan view of the operating handle portion shown in FIG. 1.
Figure 4:
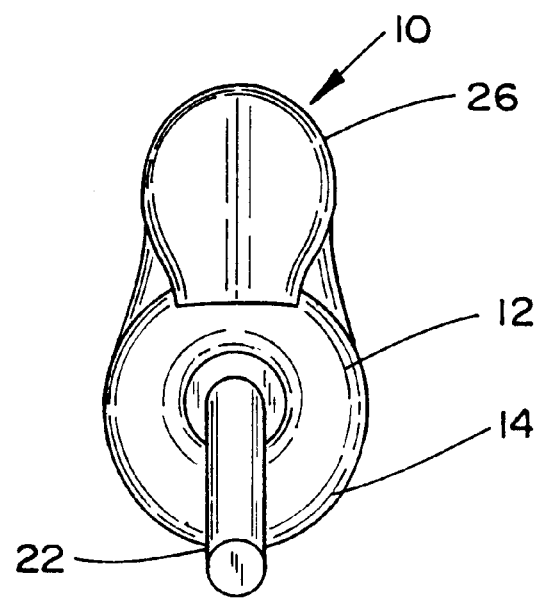
FIG. 4 illustrates a front end view of the operating handle portion show in the outer shaft connection to the tip blade and clamp assembly.
Figure 5:
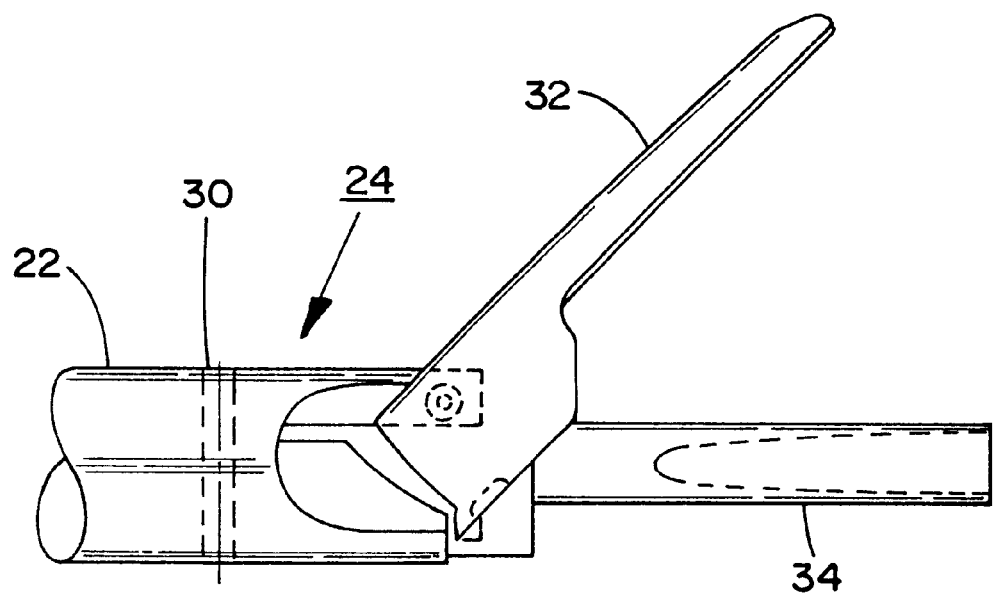
FIG. 5 illustrates, generally diagrammatically, a typical tip blade and clamp assembly portion of the ultrasonic surgical instrument.

Referring more specifically to the drawings, FIG. 1 illustrates perspectively a shroud-like handle portion 12 for an ultrasonic surgical instrument 10. The handle portion 12 is essentially of a cylindrical shape preferably, having a somewhat enlarged bulbous front end 14. Formed in the opposite sides 16 of handle portion 12, rearwardly of bulbous front end 14, are indents 18 located one each on the opposite sides of handle portion 12. The indents 18 enable the ultrasonic surgical instrument 10 to be held by a surgeon or medical practitioner, such as a physician or nurse, with a pencil grip. Within these indents 18 there is located a finger-actuatable rotator arrangement 20 for imparting rotation to a tip blade and clamp arrangement as shown in FIG. 5. The rotator arrangement 20 is operatively connected to an outer shaft 22 of the ultrasonic surgical instrument 10 extending forwardly and coaxially from the bulbous front end 14 of the handle portion 12, with rotator arrangement 20 having a 360° degree rotatability in opposite directions within handle portion 12. Rotation of rotator assembly 20 produces rotation of the outer shaft 22, to which it is connected through the intermediary of an internal drive/motor mechanism (not shown) located in the handle portion 12.

The outer shaft 22, in turn, is then connected to a tip/clamp assembly 24 so as to be able to rotate the assembly 24 about its longitudinal axis. The connection between the outer shaft 22 and the tip/clamp assembly 24 can be implemented in numerous ways, such as a pin or a hook connecting system, a threaded connection, a pivot, a wishbone collar, or the like, as is known in the technology. Similarly, the connection between the rotator arrangement 20 and the outer shaft 22 may be implemented such as through a wishbone yoke, a pin and hook system, an interference collar, and the like, wherein a crucial aspect resides in that the rotator arrangement 20, as previously mentioned, facilitates the rotation of the tip clamp assembly 24 through an angle of 360° about its longitudinal axis. The tip/clamp assembly 24 may comprise a blade and clamp arrangement for the ultrasonic surgical treatment of tissue, such as is disclosed in copending U.S. patent application Ser. No. 09/849,905, whereas the connection of outer shaft 22 to the rotator arrangement can be as in copending U.S. patent application Ser. No. 09/796,855 commonly assigned to the present assignee, and the disclosures of which are incorporated herein by reference.

A thimble-shaped lever 26 is hingedly connected to the handle portion 12 of ultrasonic surgical instrument 10 for pivoting movement at a location peripherally intermediate of and forwardly of he indents 18 in the bulbous front end 14 of the handle portion 12. Thimble-shaped lever 26 is formed so that the cup-like hollow interior 28 of the thimble-shaped lever 26 will fully receive and enclose the tip of index finger of a surgeon holding the instrument in a pencil grip. The hollow cup 28 in the thimble-shaped lever 26 is imparted an ergonomic design and configuration to provide a high degree of comfort to the user of the instrument 10. The lever 26 may be constituted of a slip-resistant material, such as a non-slip plastic to prevent unintended slippage therefrom of the finger of the user. The thimble-shaped lever 26 is operatively connected to an actuator within the outer shaft 22, with the actuator being attached to the tip/clamp and blade assembly 24 for instance through a screwthreaded connection 30, as shown in FIG. 5 by way of example. The thimble-shaped lever 26 facilitates the movement of clamp 32 on tip/clamp assembly 24 due to the operative connection between lever 26 and the actuator located within handle portion 12. There are numerous ways in which the thimble-shaped lever 26 can be operatively attached to the actuator arrangement, such as, for example, a pin, living hinge, slot slide and so forth. There are also numerous ways in which the actuator arrangement can be attached to the tip/clamp and blade assembly 24 and clamp 32 such as through a wishbone collar, a pin and hook and the like. Various embodiments of the actuator arrangement and tip/clamp assembly 24 may comprise, but are not limited to a tube and sleeve system, a hook and pin system, or a slot slide. The important aspect is that when the thimble-shaped lever 26 is tilted upwardly away from the surface of handle portion 12 by the finger of the user in the cup 28, the clamp 32 on tip/clamp assembly 24 is displaced away from blade 34. Conversely, when the thimble-shaped lever 26 is pushed down, the clamp 32 on tip/clamp and blade assembly 24 moves towards the blade 34 so as to implement a clamping action of the tissue on a patient which is located therebetween.

Simultaneously, the user may operate the rotator arrangement 20 by using his thumb and ring fingers to rotate the arrangement within the indents 18 so as to selectively impart any desired rotational movement to the tip/clamp and blade assembly 24 relative to the handle portion 12 in conjunction with the clamping action of the assembly 24.

While the invention has been particularly shown and described with respect to preferred embodiments thereof, it will be understood by those skilled in the art that the foregoing and other changes in form and details may be made therein without departing form the spirit and scope of the invention.

What is claimed is:

1. An ultrasonic surgical instrument, comprising: an end effector including relatively movable blade and clamp means for the engagement of tissue located therebetween, said end effector including ultrasonic means for propagating vibrational energy between said movable blade and clamp means;

an elongated shaft structure having a first end operatively connected to said end effector; a handle portion engageable in a pencil grip for receiving a second end of said elongated shaft structure, said second end of said elongated shaft structure being connected to operative means in said handle for imparting movement to said end effector, said operative means being adapted to receive ultrasonic energy and to transmit said ultrasonic energy to said end effector through said elongated shaft structure;

said handle portion including first finger-operated means for imparting selective clamping and releasing movement to said blade and clamp means, and second finger-operated means for imparting selective rotational displacement to said end effector; said elongated shaft structure extending from one end of said handle portion in coaxial relationship therewith, said first and second finger-operated means being spaced about the circumference of said handle portion, two indents being formed one each in the circumferential surface of said handle portion on opposite sides of and rearwardly of the location of said first finger-operated means, said indents each receiving the second finger-operated means;

said first finger-operated means comprising a pivotable lever hingedly connected to said handle portion, such that selective upward and downward pivoting of said lever respectively, imparts closing and opening movements between the clamp and blade means of said end effector so as to selectively engage and release tissue located therebetween; and wherein said lever has an essentially hollow thimble-shaped configuration to facilitate insertion therein of the index finger of a user gripping the handle portion in a pencil-like manner.

2. An ultrasonic surgical instrument as claimed in claim 1, wherein said thimble-shaped lever is constituted of a slip-resistant material so as to prevent unintended slippage of the finger of the user therefrom during operation thereof.

3. An ultrasonic surgical instrument as claimed in claim 5, wherein said slip-resistant material is constituted of a plastic material.

4. An ultrasonic surgical instrument as claimed in claim 1, wherein said second finger-operated means in each of said indents are operatively connected to actuator means for imparting a predetermined selective rotational displacement to said end effector and blade and clamp means about an axis extending coaxially with said elongated shaft structure and handle portion.

5. An ultrasonic surgical instrument as claimed in claim 4, wherein said blade and clamp means are rotatable through an angle of up to 360° about said axis in response to actuation of said second-finger operated means.

6. An ultrasonic surgical instrument as claimed in claim 4, wherein said second finger-operated means comprise a rotator arrangement responsive to actuation by, respectively, the thumb and ring finger of a user while holding the handle portion in a pencil-like grip.

7. An ultrasonic surgical instrument as claimed in claim 6, wherein said first and said second finger-operated means are separately or simultaneously actuatable by a user holding the handle portion in a pencil-like grip.

8. An ultrasonic surgical instrument as claimed in claim 1, wherein said handle portion has a bulbous enlarged end portion mounting said first finger-operated means so as to impart an ergonomic configuration to said handle portion increasing the comfort level of a user of the instrument during protracted procedures.

\* \* \* \* \*